(12) United States Patent
Borate et al.

(10) Patent No.: US 8,236,840 B2
(45) Date of Patent: Aug. 7, 2012

(54) THIOPENE CONTAINING ANALOGUES OF FLUCONAZOLE AS ANTIFUNGAL AGENTS AND PROCESS FOR THEIR PREPARATION

(75) Inventors: Hanumant Bapurao Borate, Pune (IN); Sangmeshwer Prabhakar Sawargave, Pune (IN); Suleman Riyajsaheb Maujan, Pune (IN); Mohan Anand Chandavarkar, Mumbai (IN); Sharangi Ravinda Vaiude, Mumbai (IN); Vinay Anant Joshi, Mumbai (IN)

(73) Assignees: Council of Scientific & Industrial Research, New Delhi (IN); FDC Limited, Maharashtra (IN)

( * ) Notice: Subject to any disclaimer, the term of this patent is extended or adjusted under 35 U.S.C. 154(b) by 49 days.

(21) Appl. No.: 13/058,358

(22) PCT Filed: Oct. 1, 2009

(86) PCT No.: PCT/IN2009/000543
§ 371 (c)(1),
(2), (4) Date: Feb. 10, 2011

(87) PCT Pub. No.: WO2010/046912
PCT Pub. Date: Apr. 29, 2010

(65) Prior Publication Data
US 2011/0144171 A1    Jun. 16, 2011

(30) Foreign Application Priority Data
Oct. 3, 2008 (IN) .......................... 2132/MUM/2008

(51) Int. Cl.
*A61K 31/41* (2006.01)
*A61K 31/4196* (2006.01)
*A61P 31/10* (2006.01)
*C07D 409/12* (2006.01)
(52) U.S. Cl. ................... 514/383; 514/438; 548/262.2; 548/266.6; 549/79
(58) Field of Classification Search ............. 514/383, 514/438; 548/262.2, 266.6; 549/79
See application file for complete search history.

(56) References Cited
OTHER PUBLICATIONS

Konosu, et al., Chem. Pharm. Bull., 1991, 39(10), pp. 2581-2589.*
N. Lebouvier et al., Synthesis and Antifungal Activities of New Fluconazole Analogues with Azaheterocycle Moiety. Bioorganic and Medicinal Chemistry Letters. vol. 17, Aug. 1, 2007, pp. 3686-3689.
L. Meerpoel et al., Synthesis and in vitro and in Vivo Structure-Activity Relationships of Novel Antifungal Triazoles for Dermatology. Journal of Medicinal Chemistry, vol. 48, Jan. 28, 2005, pp. 2184-2193.
R.P. Dickinson et al., Novel Antifungal 2-Aryl-1-(1H-1,24-tirazol-l-yl) butan-2-ol Derivatives with High activity Against *Aspergillus fumigatus*. Bioorganic and Medicinal Chemistry Letters, vol. 6, No. 16, Aug. 20, 1996, pp. 2031-2036.
J. Bartroli et al., New Azole Antifungals. 3. Synthesis and Antifungal Activity of 3-Substituted 4-(3H)-quinazolinones. Journal of Medicinal Chemistry, vol. 41, No. 11, Apr. 29, 1998, pp. 1869-1882.
Zhao et al., Design, Synthesis, 1H-Tiazole Derivatives Based on the Structure of the Active Site of Fungal Lanosterol 14 Alpha Demethylase (CYP51), Chemistry & Biodiversity, vol. 4, (2007), pp. 1472-1479.
Heravi et al., Synthesis of Some New Propanol Derivatives Analogous to Fluconazole, Phosphorus, Sulfur, and Silicon, vol. 179, (2004) pp. 2329-2334.

* cited by examiner

*Primary Examiner* — Susannah Chung
(74) *Attorney, Agent, or Firm* — Kramer/Amado, P.C.

(57) ABSTRACT

The present invention discloses novel compounds of the Formula (1), containing thiophene moieties and pharmaceutically acceptable salts thereof, methods for preparing these compounds, the use of these compounds in prevention and treatment of fungal infections, and pharmaceutical preparations containing these novel compounds.

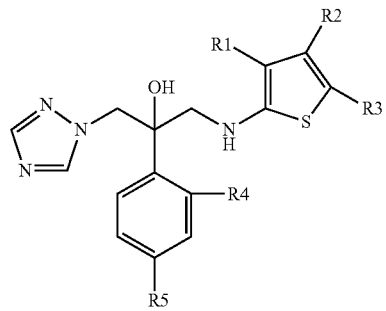

(1)

6 Claims, No Drawings

THIOPENE CONTAINING ANALOGUES OF FLUCONAZOLE AS ANTIFUNGAL AGENTS AND PROCESS FOR THEIR PREPARATION

TECHNICAL FIELD OF THE INVENTION

The present invention relates to novel compounds of the Formula (1) containing thiophene moieties and pharmaceutically acceptable salts thereof, method for preparing these compounds and the use of these compounds as antifungal agents.

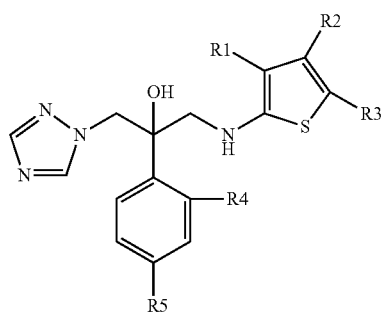

Formula 1

BACKGROUND AND PRIOR ART

Fungal infections affect most of the people sometime or other in life and create major problems in treatment of immunocompromised patients and those suffering from AIDS. The total number of these types of patients is increasing in recent years and it has become the need of the hour to have effective antifungal agents. The current antifungal agents belong to various groups like polyenes, allylamines, azoles, glucan synthesis inhibitors etc. Fluconazole is an important member of the family of azole antifungals as it is orally active and has low toxicity but its extensive use has resulted in emergence of fluconazole-resistant fungal strains. It is therefore necessary to develop analogues of fluconazole effective against resistant strains. Worldwide efforts to obtain fluconazole analogues effective against resistant strains have resulted in synthesis of many novel azole antifungals but the synthesis of ideal antifungal agent is yet to be achieved.

The structure-activity relationship studies have shown that presence of one triazole ring, halogenated phenyl ring and tertiary alcoholic oxygen functionality in fluconazole is necessary for its activity. The present invention seeks to provide novel azoles and process thereof as an effort to come up with antifungal agents with broad spectrum of antifungal activity. Fluconazole analogues have been reported to exhibit antifungal activity in the literature. Some of the references describing synthesis and antifungal activity of fluconazole analogues are:
Chemistry and Biodiversity 4, 1472-9 (2007); Bioorg Med Chem Lett 17 (13), 3686-9 (2007); J Med Chem 48 (6), 2184-93 (2005); Phosphorus Sulfur and Silicon 179, 2329-34 (2004).

The compounds described in the present invention are novel compounds with enhanced antifungal activity and hence the protection is sought for the same.

OBJECTS OF THE INVENTION

The primary objective of the present invention is to provide compounds of Formula (1), containing thiophene moieties with enhanced antifungal activity.

Another objective of the present invention is to provide the process for the preparation of the antifungal compounds of formula 1.

SUMMARY OF THE INVENTION

Accordingly, to meet the above stated objective, the present invention discloses novel fluconazole analogues of Formula (1) containing thiophene moieties, which are useful as enhanced antifungal compounds.

In one aspect, the invention provides novel compounds of formula (1), wherein, R1 is CN or COOR' (wherein R'=methyl or ethyl), R2 and R3 may be the same or different and each represents a hydrogen, alkyl group of linear or branched chain of 1 to 20 carbon atoms or cycloalkyl group with 3 to 10 carbon atoms; R4 and R5 may be the same or different and each represents a hydrogen or halogen selected from fluorine, chlorine, or bromine.

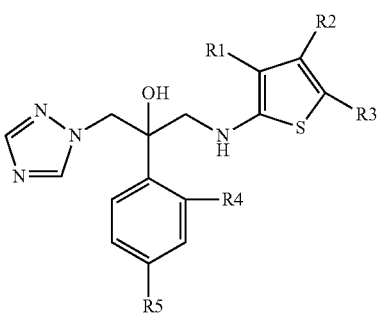

Formula 1

In another aspect, the invention provides a process for the preparation of the compounds of Formula (1). Accordingly, the present invention describes a general process for the preparation of compounds of the Formula (1) wherein R1, R2, R3, R4 and R5 are as defined above, which comprises reacting substituted alkyl 2-aminothiophene-3-carboxylates or substituted 2-aminothiophene-3-carbonitriles of the Formula (2) with formic acid and ammonium acetate to collect the corresponding substituted alkyl 2-formylaminothiophene-3-carboxylates or substituted 2-formylaminothiophene-3-carbonitriles of the Formula (3), followed by reacting the compounds of the Formula (3) with epoxide of the Formula (4) in presence of a suitable base, optionally in presence of a phase transfer agent, to obtain the compounds of the Formula 1.

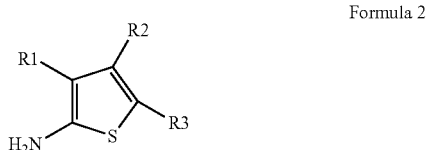

Formula 2

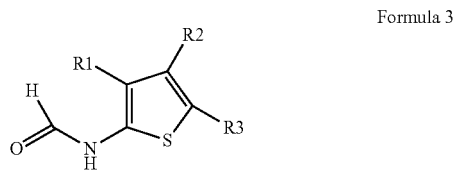

Formula 3

Formula 4

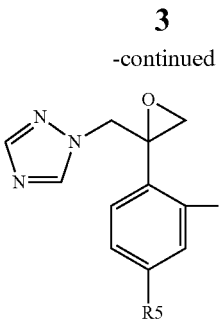

In yet another aspect, the invention discloses the use of the compounds of Formula 1 as antifungal agents.

In yet another aspect, the invention discloses a pharmaceutical preparation which comprises a compound of formula 1 in association with at least one pharmaceutical excipients.

DETAILED DESCRIPTION

The invention will now be described in detail in connection with certain preferred and optional embodiments, so that various aspects thereof may be more fully understood and appreciated.

According to the present invention, there are provided novel antifungal compounds of Formula (1). These compounds are active against fungi and can be used in pharmaceutical preparations as active agents.

In a preferred embodiment, there are provided the novel compounds of Formula (1), wherein, R1 is CN or COOR' (wherein R'=methyl or ethyl), R2 and R3 may be the same or different and each represents a hydrogen, alkyl group of linear or branched chain of 1 to 20 carbon atoms or cycloalkyl group with 3 to 10 carbon atoms; R4 and R5 may be the same or different and each represents a hydrogen or halogen selected from fluorine, chlorine or bromine.

In another preferred embodiment, the invention describes process for preparation of the compounds of formula (1). The compounds of the present invention may be prepared by adapting the route depicted in Scheme 1. As depicted in Scheme 1, the compounds of Formula (2) are converted to the compounds of Formula (3), wherein R1, R2 and R3 are as defined above. In a further step, the compounds of Formula (3) are converted to the compounds of Formula (1) by reacting with the compounds of Formula (4), wherein R4 and R5 may be the same or different and each represents a hydrogen or halogen selected from fluorine, chlorine or bromine.

Scheme 1

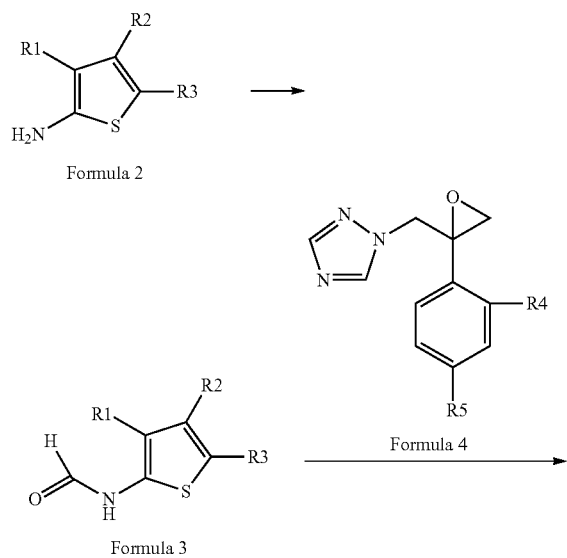

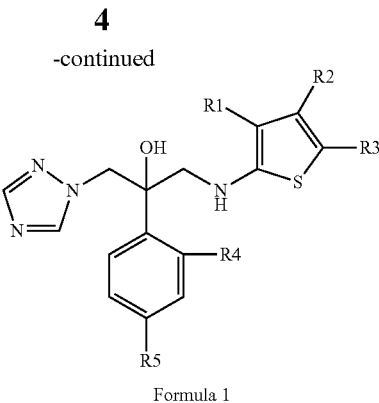

Formula 1

Accordingly, the general process for the preparation of compounds of Formula 1 comprises steps of:

a) preparing alkyl 2-amino-4 and/or 5-substituted thiophene-3-carboxylate or 2-amino-4 and/or 5-substituted thiophene-3-carbonitrile of formula 2, wherein R1 is CN or COOR' (wherein R'=methyl or ethyl), and R2 and R3 are as defined above, by Gewald synthesis (Gewald, K. *Chem. Ber.* 1965, 98, 3571; Gewald, K.; Scmnke, E.; Bottcher, H. *Chem. Ber.* 1966, 99, 94.);

b) contacting alkyl 2-amino-4 and/or 5-substituted thiophene-3-carboxylate or 2-amino-4 and/or 5-substituted thiophene-3-carbonitrile of formula 2 with formic acid and ammonium acetate at suitable temperature to obtain the corresponding alkyl 2-formylaminothiophene-3-carboxylates or substituted 2-formylaminothiophene-3-carbonitriles of the Formula 3, wherein R1, R2 and R3 are as defined above, and c) treating the compound of Formula 3 with epoxide of Formula 4, wherein R4 and R5 are as defined above, in ethyl acetate in presence of a base optionally in presence of a phase transfer agent, to obtain the compound of Formula 1.

The suitable base as used in step (c) may be selected from potassium carbonate, cesium carbonate or sodium carbonate. The phase transfer agent may be selected from tetrabutylammonium bromide, tetrabutylammonium chloride or tetrabutylammonium bisulfate.

In another preferred embodiment, the invention discloses pharmaceutical preparations which comprise a compound of Formula 1 in association with at least one pharmaceutical excipients known in art. These excipients are added to the composition for a variety of purposes.

The pharmaceutical preparations can be selected from various dosage forms such as solid dosage form like tablets, capsules, pellets, powders soft gelatin capsules, and the like and oral liquids. The tablets can be prepared as conventional dosage forms such as immediate release, sustained release, modified release or controlled release.

The pharmaceutical compositions can be prepared using conventional techniques well known in the art.

According to another embodiment, the invention provides method for treating or preventing antifungal infections in a subject, wherein said method comprises administering therapeutically effective amounts of the compounds of formula 1 of the present invention or pharmaceutical composition comprising the same. The compound of the present invention can also be administered optionally with other actives depending on the disease conditions.

As used herein the term "therapeutically effective amount" means an amount used in the pharmaceutical preparations to achieve the desired therapeutic effect.

The amount/quantity of the compound used in pharmaceutical compositions of the present invention will vary depending upon the body weight of the patient and the mode of administration and can be of any effective amount to achieve the desired therapeutic effect.

The invention further provides use of the compounds of Formula 1 in the preparation of pharmaceutical medicament.

The invention is further illustrated with the following examples and should not be construed to limit the scope of the present invention. The features of the present invention will become more apparent from the following description of the inventive concept and the description of the preferred embodiments and appended claims.

EXAMPLE 1

General Procedure for the Synthesis of Thiophene Containing Fluconazole Analogues (1)

To a flame dried $K_2CO_3$ (13.3 g, 93.8 mmol), tetra-butylammonium bromide (TBAB, 46.9 mmol) was added followed by the addition of compound of Formula (3) (46.9 mmol) in dry ethyl acetate (100 mL). Reaction mixture was stirred at reflux for 30 min. Then epoxide of Formula (4) (46.9 mmol) dissolved in dry ethyl acetate (100 mL) was added to the refluxing mixture drop wise over a period of 10 min and stirring was continued for further 12 h at the same temperature. It was then cooled to room temperature, diluted with water (400 mL), extracted with ethyl acetate (3×200 mL), dried over $Na_2SO_4$, concentrated and purified by column chromatography to give pure compounds of Formula 1 in 74-95% yields.

Various compounds were prepared by using the general procedure described above and experimental procedures and spectral data for some of the compounds are given below.

1) Ethyl 2-[2-(2,4-difluorophenyl)-2-hydroxy-3-[1,2,4]triazol-1-yl-propylamino]-5-propyl-thiophene-3-carboxylate (1c)

To the flame dried potassium carbonate (1.14 g, 8.28 mmol), was added tetra-butyl ammonium bromide (TBAB, 1.34 g, 4.14 mmol) followed by the addition of compound 3c [Compound of Formula 3 wherein R1=COOEt, R2=H and R3=Pr] (1.0 g, 4.14 mmol) in dry ethyl acetate (10 mL). Reaction mixture was stirred at 80° C. under reflux for 30 min. Then epoxide 4a [Compound of Formula 4 wherein R4=R5=F], (0.983 g, 4.14 mmol) dissolved in dry ethyl acetate (10 mL) was added to the refluxing mixture drop wise over a period of 10 min and stirring was continued for further 12 h at the same temperature. It was then cooled to room temperature, diluted with water (40 mL), extracted with ethyl acetate (3×20 mL), dried over $Na_2SO_4$, concentrated and purified by column chromatography to give pure compound of Formula 1c (1.71 g); Yield: 92%; $^1H$ NMR (200 MHz, $CDCl_3$): δ 0.93 (t, J=8 Hz, 3H), 1.30 (t, J=8 Hz, 3H), 1.49-1.68 (m, 2H), 2.54 (t, J=8 Hz, 2H), 3.64 (s, 2H), 4.21 (q, J=8 Hz, 2H), 4.67 (d, J=14 Hz, 1H), 4.87 (d, J=14 Hz, 1H), 6.64 (s, 1H), 6.74-6.82 (m, 2H), 7.45-7.58 (m, 1H), 7.81 (s, 1H), 8.02 (s, 1H).

2) Ethyl 2-[2-(2,4-difluorophenyl)-2-hydroxy-3-[1,2,4]triazol-1-yl-propylamino]-5,6-dihydro-4H-cyclopenta[b]thiophene-3-carboxylate (1g)

To a mixture of flame dried potassium carbonate (1.15 g, 8.36 mmol) and tetra-butyl ammonium bromide (TBAB, 1.35 g, 4.18 mmol), was added compound 3g [Compound of Formula 3 wherein R1=COOEt, R1, R2=$(CH_2)_3$], (1.0 g, 4.18 mmol) in dry ethyl acetate (10 mL). Reaction mixture was stirred at 75° C. for 30 min. Then epoxide 4a [Compound of Formula 4 wherein R4=R5=F], (0.991 g, 4.18 mmol) dissolved in dry ethyl acetate (10 mL) was added drop wise over a period of 10 min and stirring was continued for further 14 h at the same temperature. It was then cooled to room temperature, diluted with water (50 mL), extracted with ethyl acetate (3×30 mL), dried over $Na_2SO_4$, concentrated and purified by column chromatography to give the pure compound of Formula 1g (1.42 g); Yield: 76%; $^1H$ NMR (200 MHz, $CDCl_3$): δ 1.22 (t, J=8 Hz, 3H), 2.13-2.27 (m, 2H), 2.59-2.75 (m, 4H), 3.60 (s, 2H), 4.10 (q, J=8 Hz, 2H), 4.61 (d, J=14 Hz, 1H), 4.76 (d, J-14 Hz, 1H), 5.37 (s, 1H), 6.67-6.77 (m, 2H), 7.47-7.54 (m, 1H), 7.67 (s, 1H), 7.98 (s, 1H).

3) 2-[2-(2,4-Difluorophenyl)-2-hydroxy-3-[1,2,4]triazol-1-yl-propylamino]-5-propyl-thiophene-3-carbonitrile (1m)

The compound of Formula 3m [Compound of Formula 3 wherein R1=CN, R2=H and R3=Pr] (2.0 g, 10.3 mmol) in dry ethyl acetate (20 mL) was added to a mixture of flame dried $K_2CO_3$ (2.84 g, 20.6 mmol), tetra-butyl ammonium bromide (TBAB, 3.32 g, 10.3 mmol) and dry ethyl acetate (50 ml). Reaction mixture was stirred at 70° C. for 30 min and then epoxide 4a (2.44 g, 10.3 mmol) dissolved in dry ethyl acetate (20 mL) was added drop wise over a period of 10 min and stirring was continued for further 12 h at the same temperature. It was then cooled to room temperature, diluted with water (100 mL), extracted with ethyl acetate (3×50 mL), dried over $Na_2SO_4$, concentrated and purified by column chromatography to give pure compound of the Formula 1m (3.74 g); Yield: 90%; $^1H$ NMR (200 MHz, $CDCl_3$): δ 0.89 (t, J=7 Hz, 3H), 1.43-1.61 (m, 2H), 2.50 (t J=7 Hz, 2H), 3.65 (bs, 2H) 4.68 (d, J=14 Hz, 1H), 4.81 (d, J=14 Hz, 1H), 5.07 (bs, 1H), 6.30 (s, 1H), 6.68-6.82 (m, 2H), 7.40-756 (m, 1H), 7.79 (s, 1H), 8.06, (s, 1H).

4) 2-[2-(2,4-Difluorophenyl)-2-hydroxy-3-[1,2,4]triazol-1-yl-propylamino]-5,6-dihydro-4H-cyclopenta[b]thiophene-3-carbonitrile (1o)

To a flame dried $K_2CO_3$ (1.43 g, 10.41 mmol), tetra-butyl ammonium bromide (TBAB, 1.68 g, 5.20 mmol) was added followed by the addition of compound 3o [Compound of Formula 3 wherein R1=CN, R2,R3=$(CH_2)_3$] (1.0 g, 5.20 mmol) in dry ethyl acetate (20 mL). Reaction mixture was stirred at 80° C. for 30 min. Then epoxide 4a (1.68 g, 5.20 mmol) dissolved in dry ethyl acetate (10 mL) was added to the refluxing mixture drop wise over a period of 10 min and stirring was continued for further 11 h at the same temperature. It was then cooled to room temperature, diluted with water (60 mL), extracted with ethyl acetate (3×40 mL), dried over $Na_2SO_4$, concentrated and purified by column chromatography to give pure compound of Formula 1o (1.94 g); Yield: 93%; $^1H$ NMR (200 MHz, $CDCl_3$): δ 2.20-2.38 (m, 2H), 2.57-2.71 (m, 4H), 3.59 (d, J=14 Hz, 1H), 3.68 (d, J=14 Hz, 1H), 4.67 (d, J=14 Hz, 1H), 4.82 (d, J=14 Hz, 1H), 6.68-6.82 (m, 2H), 7.40-7.52 (m, 1H), 7.80 (s, 1H), 8.06 (s, 1H).

5) Ethyl 2-[2-(2,4-difluorophenyl)-2-hydroxy-3-[1,2,4]triazol-1-yl-propylamino]-5-methyl-thiophene-3-carboxylate (1a)

Yield: 87%; $^1H$ NMR (200 MHz, $CDCl_3$): δ 1.25 (t, J=8 Hz, 3H), 2.20 (s, 3H), 3.61 (s, 2H), 4.16 (q, J=8 Hz, 2H), 4.63

(d, J=14 Hz, 1H), 4.79 (d, J=14 Hz, 1H), 5.11(s, 1H), 6.58 (s,1H) 6.68-6.80 (m, 2H), 7.42-7.54 (m, 1H), 7.72 (s, 1H), 8.00 (s, 1H).

6) Ethyl 2-[2-(2,4-difluorophenyl)-2-hydroxy-3-[1,2,4]triazol-1-yl-propylamino]-5-ethyl-thiophene-3-carboxylate (1b)

Yield: 85%; $^1$H NMR (200 MHz, CDCl$_3$): δ 1.16-1.32 (m, 6H), 2.58 (q, J=8 Hz, 2H), 3.61 (s, 3H), 4.18 (q, J=8 Hz, 2H), 4.65 (d, J=14 Hz, 1H), 4.83 (d, J=14 Hz, 1H), 6.60 (s, 1H), 6.71-6.80 (m, 2H), 7.44-7.57 (m, 1H), 7.76 (s, 1H), 8.01 (s, 1H).

7) Ethyl 2-[2-(2,4-difluorophenyl)-2-hydroxy-3[1,2,4]triazol-1-yl-propylamino]-5-heptyl-thiophene-3-carboxylate (1d)

Yield: 82%; $^1$H NMR (200 MHz, CDCl$_3$+CCl$_4$): δ 0.88 (t, J=6 Hz, 3H), 1.24-1.34 (m, 12H), 1.64-1.66 (m, 2H), 2.55 (t, J=6 Hz, 2H), 3.63 (s, 2H) 4.20 (q, J=8 Hz, 2H), 4.67 (d, J=14 Hz, 1H), 4.85 (d, J=14 Hz, 1H), 4.96 (s, 1H), 6.61 (s, 1H), 6.72-6.82 (m, 2H), 7.46-7.59 (m, 1H), 7.79 (s, 1H), 8.05 (s, 1H).

8) Ethyl 5-n-decyl-2-[2-(2,4-difluorophenyl)-2-hydroxy-3-[1,2,4]triazol-1-yl-propylamino]-thiophene-3-carboxylate (1e)

Yield: 84%; $^1$H NMR (200 MHz, CDCl$_3$): δ 0.88 (t, J=6 Hz, 3H), 1.12-1.36 (m,17H), 1.46-1.64 (m, 2H), 2.56 (t, J=8 Hz, 2H), 3.65 (bs, 2H) 4.21 (q, J=6 Hz, 2H), 4.69 (d, J=14 Hz, 1H), 4.89 (d, J=14 Hz, 1H), 6.63 (s, 1H), 6.71-6.84 (m, 2H), 7.46-7.59 (m, 1H), 7.84 (s, 1H), 8.10 (s, 1H).

9) Ethyl 5-(3-benzyloxypropyl)-2-[2-(2,4-difluorophenyl)-2-hydroxy-3-[1,2,4]triazol-1-yl-propylamino]-thiophene-3-carboxylate (1f)

Yield: 80%; $^1$H NMR (200 MHz, CDCl$_3$): δ 1.20 (t, J=8 Hz, 3H), 1.72-1.85 (m, 2H). 2.60 (t, J=8 Hz, 2H), 3.40 (t, J=6 Hz, 2H), 3.55 (s, 2H) 4.06-4.17 (m, 2H), 4.40 (s, 2H), 4.56 (d, J=14 Hz, 1H), 4.73 (d, J=14 Hz, 1H), 5.13 (s, 1H), 6.56 (s, 1H), 6.61-6.72 (m, 2H), 7.16-7.26 (m, 5H), 7.36-7.48 (m, 1H), 7.69 (s, 1H), 7.92 (s, 1H).

10) Ethyl 2-[2-(2,4-difluorophenyl)-2-hydroxy-3-[1,2,4]triazol-1-yl-propylamino]-4,5,6,7-tetrahydrobenzo[b]thiophene-3-carboxylate (1h)

Yield: 78%; $^1$H NMR (200 MHz, CDCl$_3$): δ 1.30 (t, J=8 Hz, 3H), 1.70-1.78 (m, 4H), 2.48-2.56 (m, 4H), 3.65 (s, 2H), 4.20 (q, J=8 Hz, 2H), 4.68 (d, J=14 Hz, 1H), 4.89 (d, J=14 Hz, 1H), 4.96 (s, 1H), 6.73-6.83 (m, 2H), 7.45-7.57 (m, 1H), 7.84 (s, 1H), 8.15 (s, 1H).

11) Ethyl 2-[2-(2,4-difluorophenyl)-2-hydroxy-3-[1,2,4]triazol-1-yl-propylamino]-5,6,7,8-tetrahydro-4H-cyclohepta[b]thiophene-3-carboxylate (1i)

Yield: 77%; $^1$H NMR (200 MHz, CDCl$_3$): δ 1.32 (t, J=8 Hz, 3H), 1.55-1.83 (m, 6H), 2.52-2.63 (m, 2H), 2.91-3.01 (m, 2H), 4.24 (q, J=7 Hz, 2H), 4.72 (d, J=14 Hz, 1H), 4.92 (d, J=14 Hz, 1H), 6.71-6.90 (m, 2H), 7.44-7.58 (m, 1H), 7.89 (s, 1H), 8.26 (s, 1H).

12) Ethyl 2-[2-(2,4-difluorophenyl)-2-hydroxy-3-[1,2,4]triazol-1-yl-propylamino]-5-hexyl-4-methyl-thiophene-3-carboxylate (1j)

Yield: 85%; $^1$H NMR (200 MHz, CDCl$_3$): δ 0.89 (bs, 3H), 1.17-1.36 (m, 9H), 1.45-1.56 (m, 2H), 2.17 (s, 3H), 2.55 (t, J=8 Hz, 2H), 3.67 (bs,2H), 4.24 (q, J=8 Hz, 2H), 4.71 (d, J=16 Hz, 1H), 4.89 (d, J=16 Hz, 1H), 6.72-6.84 (m, 2H), 7.49-7.58 (m, 1H), 7.84 (s, 1H), 8.12 (s, 1H).

13) 2-[2-(2,4-Difluorophenyl)-2-hydroxy-3-[1,2,4]triazol-1-yl-propylamino]-5-methyl-thiophene-3-carbonitrile (1k)

Yield: 91%; $^1$H NMR (200 MHz, CDCl$_3$): δ 2.29 (s, 3H), 3.68 (bs, 2H), 4.71 (d, J=14 Hz, 1H), 4.88 (d, J=14 Hz, 1H), 5.44 (bs, 1H), 6.36 (s, 1H), 6.72-6.89 (m, 2H), 7.45-7.60 (m,1H), 7.88 (s, 1H), 8.09 (s, 1H).

14) 2-[2-(2,4-Difluorophenyl)-2-hydroxy-3-[1,2,4]triazol-1-yl-propylamino]-5-ethyl-thiophene-3-carbonitrile (1l)

Yield: 89%; $^1$H NMR (200 MHz, CDCl$_3$): δ 1.22 (t, J=8 Hz, 3H), 2.62 (q, J=8 Hz, 2H), 3.59-3.70 (m, 2H) 4.67 (d, J=14 Hz, 1H), 4.87 (d, J=14 Hz, 1H), 5.25 (bs, 2H), 6.38 (s, 1H), 6.71-6.88 (m, 2H), 7.47-758 (m, 1H), 7.86, (s, 1H), 7.93 (s, 1H).

15) 2-[2-(2,4-Difluorophenyl)-2-hydroxy-3-[1,2,4]triazol-1-yl-propylamino]-5-pentyl-thiophene-3-carbonitrile (1n)

Yield: 92%; $^1$H NMR (200 MHz, CDCl$_3$): δ 0.89 (t, J=7 Hz, 3H), 1.20-1.34 (m, 4H), 1.49-1.60 (m, 2H), 2.55 (t, J=8 Hz, 2H), 3.66 (bs, 2H), 4.72 (d, J=14 Hz, 1H), 4.86 (d, J=14, 1H), 6.33 (s,1H), 6.72-6.84 (m, 2H), 7.40-7.53 (m, 1H), 7.87 (s, 1H), 8.20 (s, 1H).

16) Ethyl 2-[2-(2,4-dichlorophenyl)-2-hydroxy-3-[1,2,4]triazol-1-yl-propylamino]-5-propyl-thiophene-3-carboxylate (1p)

Yield: 75%; $^1$H NMR (200 MHz, CDCl$_3$): δ 0.95 (t, J=7 Hz, 3H), 1.32 (t, J=7 Hz, 3H), 1.51-1.67 (m, 2H), 2.56 (t, J=7 Hz, 2H), 3.77 (d, J=14 Hz, 1H), 3.96 (d, J=14 Hz, 1H), 4.23 (q, J=7 Hz, 2H), 4.71 (d, J=14 Hz, 1H), 5.41 (d, J=14 Hz, 1H), 6.65 (s, 1H) 7.16 (dd, J=2 Hz, 1H), 7.34 (d, J=2 Hz, 1H), 7.65 (d, J=8 Hz, 1H), 7.84 (s, 1H) 8.08 (s, 1H).

17) Ethyl 2-[2-(4-fluorophenyl)-2-hydroxy-3-[1,2,4]triazol-1-yl-propylamino]-5-propyl-thiophene-3-carboxylate (1q)

Yield: 78%; $^1$H NMR (200 MHz, CDCl$_3$): δ 0.93 (t, J=7 Hz, 3H), 1.27 (t, J=7 Hz, 3H), 1.45-2.68 (m, 2H), 2.53 (t, J=7 Hz, 2H), 3.45 (d, J=14 Hz, 1H), 3.60 (d, J=14 Hz, 1H), 4.18 (q, J=7 Hz, 2H), 4.54 (d, J=14 Hz, 1H), 4.65 (d, J=14 Hz, 1H), 6.63 (s, 1H) 6.95-7.07 (m, 2H), 7.34-7.43 (m, 2H), 7.85 (s, 1H) 8.08 (s, 1H).

18) Ethyl 2-[2-(4-bromophenyl)-2-hydroxy-3-[1,2,4]triazol-1-yl-propylamino]-5-propyl-thiophene-3-carboxylate (1r)

Yield: 74%; $^1$H NMR (200 MHz, CDCl$_3$): δ 0.96 (t, J=7 Hz, 3H), 1.32 (t, J=7 Hz, 3H), 1.51-2.72 (m, 2H), 2.56 ((t, J=7

Hz, 2H), 3.49 (d, J=12 Hz, 1H), 3.63 (d, J=12 Hz, 1H), 4.22 (q, J=7 Hz, 2H), 4.60 (d, J=14 Hz, 1H), 4.71 (d, J=14 Hz, 1H), 6.67 (s, 1H) 7.32 (d, J=8 Hz, 2H), 7.49 (d, J=8 Hz, 2H), 7.94 (s, 1H) 8.25 (s, 1H).

19) 2-[2-(2,4-Dichlorophenyl)-2-hydroxy-3-[1,2,4] triazol-1-yl-propylamino]-5-propyl-thiophene-3-carbonitrile (1s)

Yield: 95%; $^1$H NMR (200 MHz, CDCl$_3$): δ 0.93 (t, J=7 Hz, 3H), 1.48-1.65 (m, 2H), 2.54 (t, J=7 Hz, 2H), 3.83 (d, J=14 Hz, 1H), 4.02 (d, J=14 Hz, 1H), 4.92 (d, J=14 Hz, 1H), 5.44 (d, J=14 Hz, 1H), 6.34 (s, 1H) 7.16 (dd, J=2 Hz, 1H), 7.35 (d, J=2 Hz, 1H), 7.61 (d, J=8 Hz, 1H), 8.04 (s, 1H) 8.91 (s, 1H).

20) 2-[2-(4-Fluorophenyl)-2-hydroxy-3-[1,2,4]triazol-1-yl-propylamino]-5-propyl-thiophene-3-carbonitrile (1t)

Yield: 80%; $^1$H NMR (200 MHz, CDCl$_3$): δ 0.91 (t, J=7 Hz, 3H), 1.46-1.61 (m, 2H), 2.51 (t, J=8 Hz, 2H), 3.57 (bs, 2H), 4.57 (d, J=14 Hz, 1H), 4.71 (d, J=14 Hz, 1H), 5.12 (bs, 2H), 6.32 (s, 1H), 6.92-7.06 (m, 2H), 7.33-7.44 (m, 2H), 7.89 (s, 1H) 8.28 (s, 1H).

EXAMPLE 2

General Procedures for the Synthesis of Compounds of Formula (2)

Method A:
A mixture of ethyl cyanoacetate (1 eq), sulphur (1 eq), triethyl amine (0.5 eq) and a ketone or aldehyde (1 eq) was stirred at 40 to 80° C. for 10 to 24 hrs, cooled, diluted with water, extracted with ethyl acetate, dried, concentrated and purified by column chromatography to obtain the pure compounds of the Formula (2).

Method B:
A mixture of ethyl cyanoacetate (1 eq), sulphur (1 eq), morpholine (1 eq) and ketone or aldehyde (1 eq) in ethanol was stirred at 30 to 65° C. for 8 to 22 hrs, ethanol was removed on rotavapor, the reaction mixture was extracted with ethyl acetate, dried, concentrated and purified by column chromatography to get the pure compounds of the Formula (2). The methods described above were used for preparing a number of compounds of the Formula (2) some of which are given below:

1) Ethyl 2-amino-5-(3-benzyloxypropyl)-thiophene-3-carboxylate (2f)

A mixture of ethyl cyanoacetate (2.77 ml, 26 mmol), sulphur (0.83 g, 26 mmol), triethyl amine (1.82 ml, 13 mmol) and 5-benzyloxy-1-pentanal (5,00 g, 26 mmol) in DMF (40 ml) was stirred at 45-50° C. for 12 hours. It was then cooled, diluted with water (100 ml), extracted with ethyl acetate (2×100 ml), dried, concentrated and purified by column chromatography to obtain the pure ethyl 2-amino-5-(3-benzyloxypropyl)-thiophene-3-carboxylate (4.5 gm, 54%). $^1$HNMR (CDCl$_3$, 200 MHz): δ 1.34 (t, J=8 Hz, 3H), 1.80-1.96 (m, 2H), 2.70 (t, J-7 Hz, 2H), 3.51 (t, J=7 Hz, 2H), 4.25 (q, J=7 Hz, 2H), 4.51 (s, 2H), 5.80 (bs, 2H), 6.64 (s, 1H), 7.34 (bs, 5H).

2) Ethyl 2-amino-4,5,6,7-tetrahydrobenzo[b] thiophene-3-carboxylate (2h)

A mixture of ethyl cyanoacetate (1.15 g, 0.01mol), sulphur (0.32 g, 0.01 mol), triethyl amine (0.52 g, 0.005 mol) and cyclohexanone (1.0 g, 0.01 mol) in DMF (10 ml) was stirred at 55° C. for 12 hours. It was cooled, diluted with water (80 ml), extracted with ethyl acetate (2×100 ml), dried, concentrated and purified by column chromatography to obtain the pure ethyl 2-amino-4,5,6,7-tetrahydrobenzo[b]thiophene-3-carboxylate of Formula (2h) (1.13 gm, 50%). $^1$HNMR (CDCl$_3$, 200 MHz): δ 1.27 (t, J=7 Hz, 3H), 1.62-1.78 (m, 4H), 2.35-2.50 (m, 2H), 2.54-2.70 (m, 2H), 4.19 (q, J=7 Hz, 2H).

3) Ethyl 2-amino-5-n-heptyl-thiophene-3-carboxylate (2d)

Yield: 87%; $^1$HNMR (CDCl$_3$, 200 MHz): δ 0.89 (bt, J=6 Hz, 3H), 1.26-1.48 (m, 11H), 1.51-1.71 (m, 2H), 2.58 (t, J=8 Hz, 2H), 4.26 (q, J=7 Hz, 2H), 5.49 (bs, 2H), 6.63 (s, 1H).

4) Ethyl 2-amino-5,6-dihydro-4H-cyclopenta[b] thiophene-3-carboxylate (2g)

Yield: 63%; $^1$HNMR (CDCl$_3$, 200 MHz): δ 1.32 (t, J=7 Hz, 3H), 2.22-2.38 (m, 2H), 2.65-2.90 (m, 4H), 4.24 (q, J=7 Hz, 2H), 5.85 (bs, 2H).

5) Ethyl 2-amino-5-n-hexyl-4-methyl-thiophene-3-carboxylate (2j)

Yield: 84%; $^1$HNMR (CDCl$_3$, 200 MHz): δ 0.90 (bt, J=6 Hz, 3H), 1.22-1.40 (m, 9H), 1.45-1.63 (m, 2H), 2.18 (s, 3H), 2.54 (t, J=8 Hz, 2H), 4.28 (q, J=8 Hz, 2H), 5.01 (bs, 2H).

6) Ethyl 2-amino-5-n-decyl-thiophene-3-carboxylate (2e)

Yield: 71%; $^1$HNMR (CDCl$_3$, 200 MHz): δ 0.88 (bt, J=6 Hz, 3H), 1.18-1.40 (m including t at 1.33 with J=7 Hz, 17H), 1.49-1.65 (m, 2H), 2.56 (t, J=7 Hz, 2H), 4.25 (q, J=7 Hz, 2H), 5.40 (bs, 2H), 6.63 (s, 1H).

7) Ethyl 2-amino-5-n-propyl-thiophene-3-carboxylate (2c)

Yield: 82%; $^1$HNMR (CDCl$_3$, 200 MHz): δ 0.95 (t, J=7 Hz, 3H), 1.34 (t, J=7 Hz, 3H), 1.51-1.71 (m, 2H), 2.56 (t, J=7 Hz, 2H), 4.26 (q, J=7 Hz, 2H), 4.75 (bs, 2H), 6.64 (s, 1H).

8) Ethyl 2-amino-5-ethyl-thiophene-3-carboxylate (2b)

Yield: 93%; $^1$HNMR (CDCl$_3$, 200 MHz): δ 1.23 (t, J=7 Hz, 3H), 1.34 (t, J=7 Hz, 3H), 2.62 (q, J=7 Hz, 2H), 4.26 (q, J=7 Hz, 2H), 4.62 (bs, 2H), 6.64 (s, 1H).

9) 2-Amino-5-n-propyl-thiophene-3-carbonitrile (2m)

Yield: 89%; $^1$HNMR (CDCl$_3$, 200 MHz): δ 0.94 (t, J=7 Hz, 3H), 1.48-1.68 (m, 2H), 2.54 (t, J=8 Hz, 2H), 4.77 (bs, 2H) 6.34 (s, 1H).

EXAMPLE 3

General Procedure for the Synthesis of alkyl 4/5-substituted 2-formylaminothiophene-3-carboxylates and 4/5-substituted 2-formylaminothiophene-3-carbonitriles of Formula (3):

A mixture of compound of Formula (2) (0.027 mol), ammonium acetate (0.027 mol) and formic acid (0.54 mol)

was stirred at 20-140° C. for 5-15 h, cooled to room temperature and diluted with water. The precipitate obtained was filtered through Whatman filter paper, washed with excess of water followed by ethyl acetate-pet ether (15:85) to afford pure product.

A number of compounds were prepared by following the above method. Spectral data for some of the compounds are given below:

1) Ethyl 2-formylamino-5-propyl-thiophene-3-carboxylate (3c)

A mixture of compound 2c [Formula 2 wherein R1=COOEt, R2=H and R3=Pr] (5.0 g, 0.023 mol), ammonium acetate (1.80 g, 0.023 mol) and formic acid (17.70 mL, 0.469 mol) was stirred at 135-140° C. for 7 h, cooled to room temperature, diluted with water (250 mL), extracted with ethyl acetate (3×150 mL), dried over $Na_2SO_4$, concentrated and purified by column chromatography to give pure compound of Formula (3c); 5.27 g; Yield: 95%; $^1$H NMR (200 MHz, $CDCl_3$): δ 0.96 (t, J=7 Hz, 3H), 1.38 (t, J=7 Hz, 3H), 1.59-1.76 (m, 2H), 2.69 (t, J=8 Hz, 2H), 4.33 (q, J=7 Hz, 2H), 6.88 (s, 1H), 8.49 (s, 1H) 10.93 (bs, 1H).

2) Ethyl 2-formylamino-5,6-dihydro-4H-cyclopenta[b]thiophene-3-carboxylate (3g)

A mixture of compound 2g [Compound of Formula 2 wherein R1=COOEt, R2, R3=$(CH_2)_3$] (10.0 g, 0.046 mol), ammonium acetate (3.64 g, 0.060 mol) and formic acid (35.74 mL, 0.946 mol) was stirred at 130-135° C. for 8 h. It was then cooled to room temperature and diluted with water (150 mL), extracted with ethyl acetate (3×100 mL), dried over $Na_2SO_4$, concentrated and purified by column chromatography to give pure compound of Formula (3g); 10.66 g; Yield: 97%; $^1$H NMR (200 MHz, $CDCl_3$+DMSO-d6): δ 0.1.33 (t, J=8 Hz, 3H), 2.25-2.43 (m, 2H), 2.74-2.89 (m, 4H), 4.26 (q, J=8 Hz, 2H), 8.48 (s, 1H) 11.16 (bs, 1H).

3) 2-Formylamino-5-n-propyl-thiophene-3-carbonitrile (3m)

A mixture of compound 2m [Formula 2 wherein R1=CN, R2=H and R3=Pr] (5.0 g, 0.030 mol), ammonium acetate 2.31 g (0.030 mol) and formic acid 22.71 mL (0.602 mol) was stirred at 30° C. for 1 h. It was then diluted with water (250 mL). The precipitate obtained was filtered through Whatman filter paper, washed with excess of water followed by ethyl acetate-pet ether (5:95) to afford pure product of Formula (3m); 5.41 g; Yield: 93%; $^1$H NMR (200 MHz, $CDCl_3$): δ 0.68 (t, J=7 Hz, 3H), 1.25-1.45 (m, 2H), 2.40 (t, J=7 Hz, 2H), 6.36 (s, 2H) 8.14 (s, 1H), 11.19 (bs, 1H).

4) Ethyl 2-formylamino-5-methyl-thiophene-3-carboxylate (3a)

Yield: 88%; $^1$H NMR (200 MHz, $CDCl_3$): δ 1.37 (t, J=7 Hz, 3H), 2.39 (s, 3H), 4.33 (q J=7 Hz, 2H), 6.87 (s, 1H), 8.48 (s, 1H) 10.91 (bs, 1H).

5) 2-Formylamino-5-methyl-thiophene-3-carbonitrile (3k)

Yield: 81%; $^1$H NMR (200 MHz, $CDCl_3$): δ 2.77 (s, 3H), 6.40 (s, 1H), 8.17 (s, 1H) 11.23 (bs, 1H).

EXAMPLE 4

Preparation of 1-[2-(2,4-difluorophenyl)-oxiranylmethyl]-1H-[1,2,4]triazole (4a) of Formula (4) wherein R4=R5=F A mixture of 1-(2,4-difluorophenyl)-2-(1H-1,2,4-triazolyl)-ethanone (0.134 mol, 30.00 g), trimethylsulfoxonium iodide (0.201 mol, 44.40 g), and cetrimide (0.001345 mol, 0.49 g) in dichloromethane (300 mL) was stirred at room temperature for 10 min. Then a solution of KOH (0.336 mol, 18.83 g) in water (40 mL) was added to it. This mixture was refluxed at 40-45° C. for 12 h, cooled to room temperature and diluted with water (600 mL). The two layers were separated, the aqueous layer was extracted with dichloromethane (3×500 mL) and the combined organic extracts were dried over $Na_2SO_4$. After the solvent was concentrated in vacuo, the residue was subjected to chromatography on silica gel to afford pure epoxide of Formula (4) wherein R4=R5=F (27.10 g, 85%); $^1$H NMR (200 MHz, $CDCl_3$+$CCl_4$): δ 2.85 (d, J=6 Hz, 1H), 2.95 (d, J=6 Hz, 1H), 4.50 (d, J=16 Hz, 1H), 4.80 (d, J=16 Hz, 1H), 6.76-6.89 (m, 2H), 7.12-7.26 (m, 1H), 7.83 (s, 1H), 8.07 (s, 1H).

The other epoxides were prepared using same procedure.
1-[2-(2,4-Dichlorophenyl)-oxiranylmethyl]-1H-[1,2,4]triazole (4b) of Formula (4) wherein R4=R5=Cl Yield: 77%; $^1$H NMR (200 MHz, $CDCl_3$+$CCl_4$): δ 2.92 (d, J=4 Hz, 1H), 3.01 (d, J=4 Hz, 1H), 4.53 (d, J=14 Hz, 1H), 4.90 (d, J=14 Hz, 1H), 7.16-7.46 (m, 3H), 7.92 (s, 1H), 8.13 (s, 1H).

1-[2-(4-Bromophenyl)-oxiranylmethyl]-1H-[1,2,4]triazole (4c) of Formula (4) wherein R4=H, R5=Br Yield: 82%, $^1$H NMR (200 MHz, $CDCl_3$+$CCl_4$): δ 2.81 (d, J=6 Hz, 1H), 2.87 (d, J=6 Hz, 1H), 4.59 (d, J=14 Hz, 1H), 4.80 (d, J=14 Hz, 1H), 7.20 (d, J=8 Hz, 2H), 7.47 (d, J=8 Hz, 2H), 7.89 (s, 1H), 8.08 (s, 1H).

EXAMPLE 5

Antifungal Activity Testing:

The compounds of Formula 1 were tested for antifungal activity against *Candida albicans, Aspergillus niger* and *Fusarium proliferatum*. In vitro evaluation of antifungal activity was performed by determining the minimum inhibitory concentration (MIC) following standard methods (CLSI: Reference method for broth dilution antifungal susceptibility testing of yeasts; Approved standard, second edition M27-A2, 2002; CLSI: Reference method for broth dilution antifungal susceptibility testing of filamentous fungi; Approved standard M38-A, 2002). Anti-fungal susceptibility testing of these compounds of Formula 1 was done by broth dilution method using RPMI 1640 medium with MOPS buffer. Known anti-fungal agents like Fluconazole and Amphotericin-B were used as standards. End points were determined after 48 hours visually and by using spectrophotometer wherever necessary. The activity parameters are enumerated in Table 1:

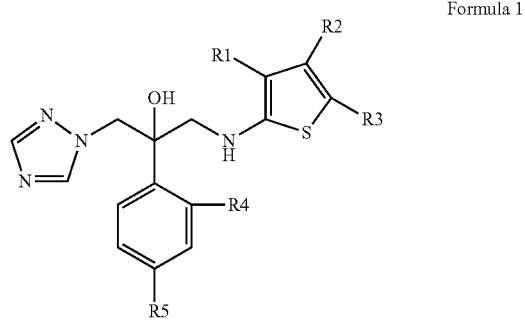

Formula 1

TABLE 1

| | | | MIC obtained by broth macro-dilution method | | |
|---|---|---|---|---|---|
| | | | Activity against organisms MIC in µg/ml | | |
| Sr No. | Compound No. | Structure 1 | *C. albicans* ATCC 24433 | *A. niger* ATCC 16404 | *F. proliferatum* ATCC 10052 |
| 1 | Fluconazole | | 1 | 128 | >128 |
| 2 | Amphotericin B | | 0.25 | 1 | 2 |
| 3 | 1a | R1 = COOEt, R2 = H, R3 = Methyl, R4 = R5 = F | 2 | >16 | >16 |
| 4 | 1b | R1 = COOEt, R2 = H, R3 = Ethyl, R4 = R5 = F | 2 | >4 | >4 |
| 5 | 1c | R1 = COOEt, R2 = H, R3 = Propyl, R4 = R5 = F | 2 | >16 | >16 |
| 6 | 1d | R1 = COOEt, R2 = H, R3 = n-Heptyl, R4 = R5 = F | >8 | >8 | >8 |
| 7 | 1e | R1 = COOEt, R2 = H, R3 = n-Decyl, R4 = R5 = F | >4 | >4 | >4 |
| 8 | 1f | R1 = COOEt, R2 = H, R3 = —(CH$_2$)$_3$—OCH$_2$Ph, R4 = R5 = F | >4 | >4 | >4 |
| 9 | 1g | R1 = COOEt, R2, R3 = —(CH$_2$)$_3$—, R4 = R5 = F | 2 | >8 | >8 |
| 10 | 1h | R1 = COOEt, R2, R3 = —(CH$_2$)$_4$—, R4 = R5 = F | 4 | >4 | >4 |
| 11 | 1i | R1 = COOEt, R2, R3 = —(CH$_2$)$_5$—, R4 = R5 = F | 8 | >8 | >8 |
| 12 | 1j | R1 = COOEt, R2 = Methyl, R3 = n-Hexyl, R4 = R5 = F | >2 | >2 | >2 |
| 13 | 1k | R1 = CN, R2 = H, R3 = Methyl, R4 = R5 = F | 0.5 | >32 | >32 |
| 14 | 1l | R1 = CN, R2 = H, R3 = Ethyl, R4 = R5 = F | 0.25 | >16 | >16 |
| 15 | 1m | R1 = CN, R2 = H, R3 = Propyl, R4 = R5 = F | 0.12 | >32 | >32 |
| 16 | 1n | R1 = CN, R2 = H, R3 = n-Pentyl, R4 = R5 = F | 0.25 | >4 | >4 |
| 17 | 1o | R1 = CN, R2, R3 = —(CH$_2$)$_3$—, R4 = R5 = F | 0.5 | >16 | >16 |
| 18 | 1p | R1 = COOEt, R2 = H, R3 = Propyl, R4 = R5 = Cl | ND | ND | ND |

TABLE 1-continued

MIC obtained by broth macro-dilution method

| | | | Activity against organisms MIC in µg/ml | | |
|---|---|---|---|---|---|
| Sr No. | Compound No. | Structure 1 | C. albicans ATCC 24433 | A. niger ATCC 16404 | F. proliferatum ATCC 10052 |
| 19 | 1q | R1 = COOEt, R2 = H, R3 = Propyl, R4 = H, R5 = F | ND | ND | ND |
| 20 | 1r | R1 = COOEt, R2 = H, R3 = Propyl, R4 = H, R5 = Br | ND | ND | ND |
| 21 | 1s | R1 = CN, R2 = H, R3 = Propyl, R4 = R5 = Cl | ND | ND | ND |
| 22 | 1t | R1 = CN, R2 = H, R3 = Propyl, R4 = H, R5 = F | ND | ND | ND |

ND—Not done,

For Fluconazole and the novel compounds of Formula 1, MIC is recorded as the concentration exhibiting 80% inhibition as compared to the positive growth control. For Amphotericin B, MIC is recorded as the concentration exhibiting complete inhibition. >16 µg/ml: The novel compounds of Formula 1 are generally tested for concentration range from 0.03 µg/ml to the concentration till it was in solution (For e.g.: Back precipitation observed at 128-32 µg/ml, Concentration for assay: 0.03 to 16 µg/ml).

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

We claim:
1. An antifungal compound of the Formula 1:

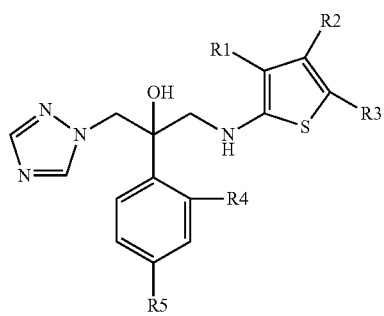

Formula 1 wherein:
R1 is CN or COOR', where R' is lower alkyl;
R2 and R3 are the same or different, where R2 and R3 are each independently selected from the group consisting of hydrogen, an alkyl group having a linear or branched chain of 1 to 20 carbon atoms, and a cycloalkyl group having 3 to 10 carbon atoms; and
R4 and R5 are the same or different, where R4 and R5 are each independently selected from the group consisting of hydrogen, fluorine, chlorine and bromine.

2. The compound of claim 1, wherein R' is methyl or ethyl.

3. A process of preparing compounds of Formula 1:

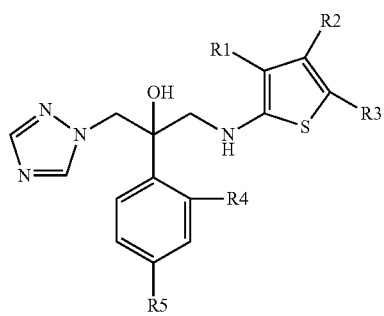

Formula 1 wherein:
R1 is CN or COOR', where R' is lower alkyl;
R2 and R3 are the same or different, where R2 and R3 are each independently selected from the group consisting of hydrogen, an alkyl group having a linear or branched chain of from 1 to 20 carbon atoms, and a cycloalkyl group having from 3 to 10 carbon atoms; and
R4 and R5 are the same or different, where R4 and R5 are each independently selected from the group consisting of hydrogen, fluorine, chlorine and bromine;
said process comprising:
a) obtaining a compound of formula 2:

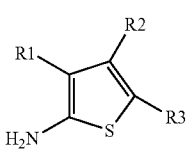

Formula 2 wherein R1, R2, and R3 are as defined above;
b) reacting the compound of formula 2 with formic acid and ammonium acetate to obtain a compound of Formula 3:

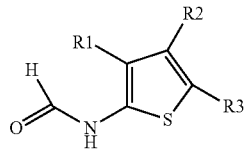

Formula 3 wherein R1, R2 and R3 are as defined above; and
c) treating the compound of Formula 3 with an epoxide of Formula 4:

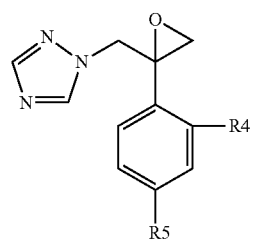

Formula 4 wherein R4 and R5 are as defined above, in the presence of a base to obtain the compound of Formula 1.

4. The method of claim 3, wherein said obtaining comprises preparing the compound of formula 2 by the Gewald synthesis.

5. A pharmaceutical composition comprising the antifungal compound according to claim 1, in association with at least one pharmaceutical excipient.

6. A method for treating or preventing a fungal infection in a subject, which comprises administering to said subject an effective amount of the antifungal compound according to claim 1 in association with pharmaceutical excipients.

* * * * *